United States Patent [19]

Cheng

[11] Patent Number: 4,870,987
[45] Date of Patent: Oct. 3, 1989

[54] RELATING TO A FLOW REGULATOR FOR INTRAVENOUS INJECTION DEVICE

[76] Inventor: Ton-Lin Cheng, No. 23, Lane 70, Min-Tsu 2nd Rd., Kaohsiung, Taiwan

[21] Appl. No.: 223,013

[22] Filed: Jul. 22, 1988

[51] Int. Cl.$^4$ ............................................. F16K 31/22
[52] U.S. Cl. .................................... 137/192; 137/399; 137/433; 604/127; 604/254
[58] Field of Search ........................ 137/192, 433, 399; 604/254, 127

[56] References Cited

U.S. PATENT DOCUMENTS

| | | | |
|---|---|---|---|
| 1,250,410 | 11/1916 | Tenney | 604/127 |
| 2,465,784 | 3/1949 | Cofoid | 604/254 X |
| 2,989,052 | 6/1961 | Browan | 137/192 X |
| 3,227,173 | 1/1966 | Bernstein | 604/127 |
| 3,738,361 | 6/1973 | Price | 137/192 X |
| 4,055,176 | 10/1977 | Lindquist | 604/254 X |
| 4,056,116 | 11/1977 | Carter | 604/254 X |
| 4,640,306 | 2/1987 | Fan | 604/254 X |

Primary Examiner—Alan Cohan
Attorney, Agent, or Firm—Banner, Birch, McKie & Beckett

[57] ABSTRACT

A flow regulator comprises a float valve body provided in an inner container which in turn is fitted in a lower portion of an outer container. The float body has an elongated slender upper portion which is suddenly restricted at an upper side and an elongated tapered lower portion. The slender upper portion extends through a central opening of a first plate at the top end of the inner container. The tapered lower portion passes through a valve seat of a second plate placed below the first plate and extends beyond a restricted tubular bottom end of the inner container. A flexible tube is sleeved on said tubular bottom end and receives the end of the float body. By moving the flexible tube, the float body can be moved away from the valve seat. A further valve seat may be formed in the tubular bottom end of the inner container.

3 Claims, 2 Drawing Sheets

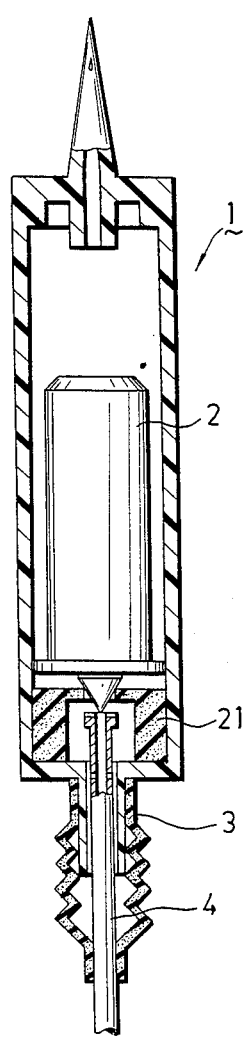
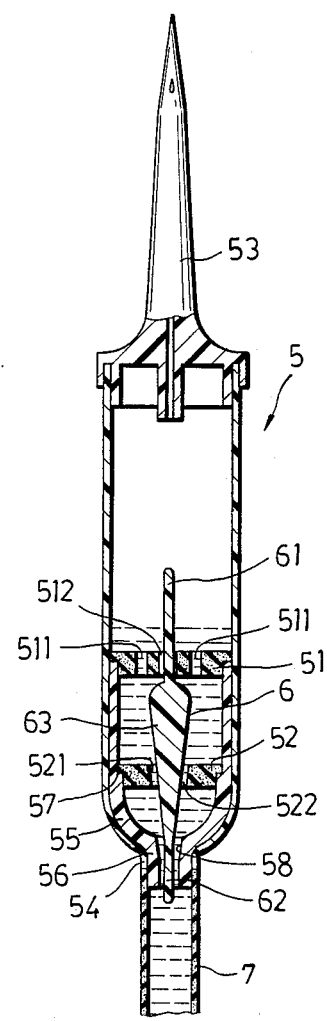
FIG. 1
PRIOR ART
FIG. 2

RELATING TO A FLOW REGULATOR FOR INTRAVENOUS INJECTION DEVICE

BACKGROUND OF THE INVENTION

This invention relates to a flow regulator for an intravenous injection device and particularly to a flow regulator which includes an improved float body having an elongated slender upper portion which is restricted suddenly at the upper side of the float body and an elongated tapered lower portion to be seated against two valve seats.

Various forms of flow regulator for intravenous injection devices are provided in the art. Examples of the flow regulators are described, in U.S. Pat. Nos. 1,205,410, 3,227,173, 3,465,784, 4,055,176 and 4,056,116. FIG. 1 shows one of conventional flow regulators which has a container 1, a float body 2 to be seated against a valve seat formed in a rubber member 21, a flexible tube 3 having a bellows like construction connected to the bottom end of the container 1, and a pushing rod 4 inserted in the tube 3. Although the valve seat of this device is effective for providing a good sealing effect, the device has a disadvantage in that the presence of the pushing rod requires a greater number of steps for assembly.

SUMMARY OF THE INVENTION

An object of the invention is to provide a flow regulator which has a float body with an improved construction by which the float body can be easily seated against the valve seat and removed from the valve seat without using a pushing rod.

Another object of the invention is to provide a flow regulator with a more powerful sealing effect than that of conventional flow regulators.

According to the present invention, a flow regulator comprises: a cylindrical outer container; an inner container fitted in the lower portion of the outer container, having an open top end and a restricted tubular bottom end; a first plate with a central opening to close the open top end of the inner container; a second plate positioned in the inner container below the first plate, the second plate having a first valve seat; a flexible tube sleeved on the tubular bottom end of the inner container; and a float valve body provided in the inner container and having an elongated slender upper portion which is suddenly restricted at the upper side of the float body, and an elongated tapered lower portion at the lower side of the float body, the slender upper portion extending through the central opening, the tapered lower portion having an upper portion passing through the valve seat and an end portion extending beyond the tubular bottom end of the inner container and then entering the flexible tube, the upper portion of the tapered lower portion having a first surface portion to contact tightly the first valve seat. Alternatively, the regulator may be further provided with a second valve seat at the tubular bottom end of the inner container to make a tight contact with a second surface portion of the tapered lower portion of the float body.

The exemplary preferred embodiment will be described in detail with reference to the accompanying drawings, in which:

BRIEF DESCRIPTION OF THE DRAWINGS

FIG. 1 is a view of a flow regulator in the prior art;

FIG. 2 is a view of the flow regulator of the present invention;

DETAILED DESCRIPTION OF THE PREFERRED EMBODIMENT

Figure 3:
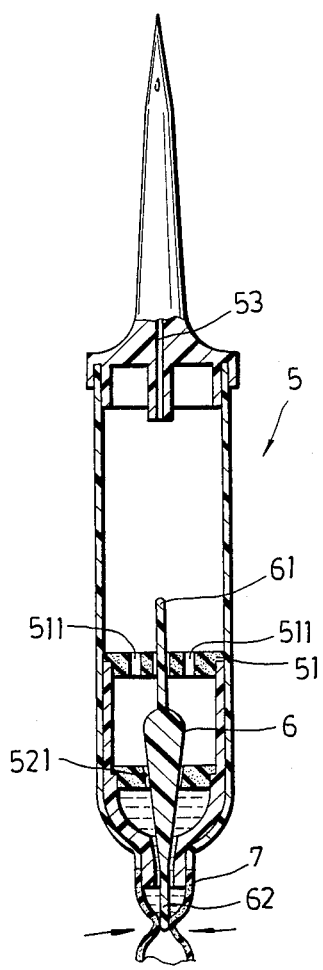
FIG. 3 is a view of the flow regulator of FIG. 2 in which the flexible tube is squeezed to move upward the float body.
Figure 4:
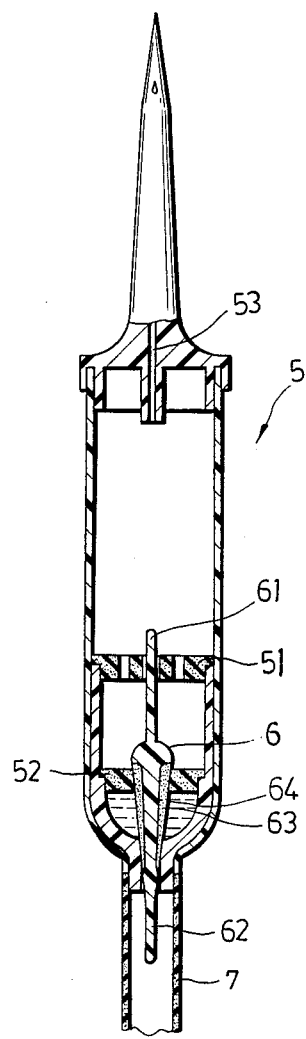
FIG. 4 shows the flow regulator with a modified float body which is in a closing position.

Referring to FIGS. 2 to 4, a preferred embodiment of the present invention is shown, having a cylindrical container 5 which is made of a plastic material and has a cylindrical wall. The wall has at its top side a spike member 53 incorporating an inlet passage, and at its bottom side a restricted tubular outlet portion 54.

At the inside of the container 5 is an inner container 55 which is also made of a plastic material and has a wall conforming to shape of the lower portion of the outer wall of the container 5 as well as a restricted tubular outlet portion 56. The wall of the inner container 55 abuts the wall of the container 5. The outlet portion 56 is fitted into the outlet portion 54 of the outer container 5 and extends beyond the outlet portion 54. The inner side of the tubular outlet portion 56 is further provided with a valve seat 58 at which the lower end portion of the float body 6 can be seated.

The inner container further has an open top end remote from the top end of the outer container 5. Below the open top end, an annular shoulder 57 is provided at the inner side of the wall of the inner container 55. A flexible tube 7 is sleeved onto the tubular outlet portion 56 of the inner container. The tube 7 can be squeezed by fingers and is slightly extendible and contractible in the longitudinal direction thereof.

A cover plate 51 which is made of a rubber is provided to close sealingly the open top end of the inner container 55. Openings 511 and a central opening 512 are provided in the cover plate 51. A further plate 52 which is made of a rubber is positioned at the annular shoulder 57. A valve seat 521 is formed in the plate 52.

A float body 6 is provided in the inner container 55, having an elongated slender upper portion 61 restricted suddenly at the upper side of the float body 6 and an elongated tapered lower portion including an end portion 62 and an upper portion 63. The upper portion 61 of the float body 6 extends through the central opening 512 of the cover plate 51. The upper portion 63 of the tapered portion passes through the valve seat 521 of the plate 52, and the end portion 62 extends beyond the tubular outlet portion 56 of the inner container and enters the flexible tube 7. By squeezing and moving the flexible tube 7, the end portion 62 of the float body 6 can be clamped and moved upward from the valve seats.

When a substantial amount of injection fluid is present in the container 5, the float valve body 6 is in its floating position, i.e. the upper portion 63 and the bottom end portion 62 of the tapered lower portion of the float body do not come in contact with the valve seats 521 and 58 respectively. However, the float valve body 6 does not move away from the valve seats since it is guided by the plates 51 at the upper side thereof and the tubular outlet portion 56 at the lower side thereof. The plate 51 prevents the float body 6 from moving upward and centers the slender portion 61. The tubular outlet portion 56 prevents the lower portion of the float body 6 from moving laterally in a large amount. When the container 5 is empty of the liquid, the float body 6 blocks the opening 522 of the plate 52 and the passage of the tubular outlet portion 56 by means of a contact surface at the portion 63 and a contact surface at the portion 62 which are seated on the valve seats 521 and 58 respectively.

The float body 6 of the present invention can be modified in such a manner that it has a sleeve member 64 around the portion 63, which is made of rubber. The sleeve member 64 provides an effective sealing contact with the valve seat;

With the invention thus explained, it is apparent that numerous modifications and variations can be made without departing from the scope of the invention. It is therefore intended that the invention be limited as indicated only in the appended claims.

What I claim is:

1. A flow regulator for an intravenous injection device comprising:
   a cylindrical outer container having a cylindrical outer wall which has a top end and a lower portion with a bottom outlet;
   an inner container disposed in said outer container and having an inner wall substantially conforming to the shape of said lower portion of said outer wall, said inner wall abutting an inner side of said lower portion of said outer wall, said inner wall having a top open end remote from said top end of said outer container and a restricted tubular bottom end extending out of said bottom outlet of said outer wall,
   a first cover plate closing said open top end of said inner container, said cover plate having a central opening,
   a second plate positioned in said inner container below said first plate, said second plate having a first valve seat;
   a flexible tube sleeved on said restricted tubular bottom end of said inner container,
   a float valve body provided in said inner container and having an elongated slender upper portion which is suddenly restricted at an upper side of said float body, and an elongated tapered lower portion at a lower side of said float body, said slender upper portion extending through said central opening, said tapered lower portion having an upper portion passing through said valve seat and an end portion extending beyond said restricted tubular bottom end of said inner container and then entering said flexible tube, said upper portion of said tapered lower portion having a first surface portion to contact tightly said first valve seat.

2. A flow regulator as claimed in claim 1, wherein said inner wall further has at its inner side an annular shoulder below said top open end of said inner container, and said second plate is positioned on said annular shoulder.

3. A flow regulator as claimed claim 1, wherein said tapered lower portion of said float valve body further has a second surface portion at said end portion of said tapered lower portion, and said restricted tubular bottom end of said inner container has a second valve seat to contact said second surface portion.

* * * * *